United States Patent
Szeto et al.

(10) Patent No.: US 10,046,017 B2
(45) Date of Patent: Aug. 14, 2018

(54) POMEGRANATE SKIN EXTRACT FOR TREATING FATTY LIVER

(71) Applicant: NESTEC S.A., Vevey (CH)

(72) Inventors: Ignatius Szeto, Beijing (CN); Peifang Zhang, Chesterfield, MO (US); Weiguo Zhang, Irving, TX (US); Junkuan Wang, Beijing (CN); Chieh Jason Chou, Chexbres (CH)

(73) Assignee: Nestec S.A., Vevey (CH)

( * ) Notice: Subject to any disclaimer, the term of this patent is extended or adjusted under 35 U.S.C. 154(b) by 133 days.

(21) Appl. No.: 15/109,723

(22) PCT Filed: Jan. 9, 2014

(86) PCT No.: PCT/CN2014/070408
§ 371 (c)(1),
(2) Date: Jul. 5, 2016

(87) PCT Pub. No.: WO2015/103760
PCT Pub. Date: Jul. 16, 2015

(65) Prior Publication Data
US 2016/0324907 A1    Nov. 10, 2016

(51) Int. Cl.
| | | |
|---|---|---|
| *A61K 36/00* | (2006.01) | |
| *A61K 36/185* | (2006.01) | |
| *A61K 31/7048* | (2006.01) | |
| *A23L 33/00* | (2016.01) | |
| *A23L 33/105* | (2016.01) | |
| *A61K 9/00* | (2006.01) | |

(52) U.S. Cl.
CPC .......... *A61K 36/185* (2013.01); *A23L 33/105* (2016.08); *A23L 33/30* (2016.08); *A61K 9/0053* (2013.01); *A61K 31/7048* (2013.01); *A23V 2002/00* (2013.01)

(58) Field of Classification Search
CPC .................................................... A61K 36/00
See application file for complete search history.

(56) References Cited

U.S. PATENT DOCUMENTS

2011/0236413 A1    9/2011 Oben

FOREIGN PATENT DOCUMENTS

| CN | 101955500 | 1/2011 |
| CN | 101974043 | 2/2011 |
| CN | 102149397 | 8/2011 |
| CN | 102180916 | 9/2011 |
| CN | 102295666 | 12/2011 |
| CN | 102641312 | 8/2012 |
| CN | 103467534 | 12/2013 |
| KR | 20130141237 A * | 12/2013 |

OTHER PUBLICATIONS

Parmar et al, Protective role of Citrus sinensis, Musa paradisiaca, and Punica granatum peels against diet-induced atherosclerosis and thyroid dysfunctions in rats. Nutrition research (2007), pp. 710-718, ISSN: 0271-5317 Source Note: Nov. 2007, v. 27, issue 11.*
Punalpin® increases the numbers of motile sperm in men with reduced semen quality: A prospective, randomized, controlled, doubleblinded trial. Human Reproduction, (Jun. 2013) vol. 28, Supp. SUPPL. 1, pp. i10-i11.*
Tan et al. "Effects of Tannin in *Punica granatum* L., on Blood Lipids and Its Protecting Liver Ability in Diabetic Rats" J. Med. Res., 2012, vol. 41, No. 10, pp. 80-82.
Cheng et al. "Experimental Study on Hypolipidemic Effect of Polyphenolic Extract from Pomegranate Peel" J. Prev. Med. Chin. PLA, 2005, vol. 23, No. 3, pp. 160-163.
Liang et al. "Effects of Pomegranate Peel Polyphenols(PPPs) on the Expression of HMG-CoA Reductase mRNA of Human L-02 Hepatocyte" Journal of Food Science and Biotechnology, 2013, vol. 32, No. 9, pp. 957-961.
CC Lin, et al. Antioxidant and hepatoprotective effects of punicalagin and punicalin on acetaminophen-induced liver damage in rats. Phytother Res 15:206 (2001).†
Zheng-Jie Xu, et al. Characterization of high-fat diet-induced, non-alcoholic steatohepatitis with fibrosis in rats. Dig Dis Sci 55:931 (2010).†
Marie-Soleil Gauthier, et al. Time course of the development of non-alcoholic hepatic steatosis in response to high-fat diet-induced obesity in rats. Br J Nutr 95:273 (2006).†
Xuan Zou, et al. Mitochondrial dysfunction in obesity-associated nonalcoholic fatty liver disease: the protective effects of pomegranate with its active component punicalagin. Antiox Redox Signaling 21:1557 (2014), submitted Jul. 15, 2013. Entire paper.†

\* cited by examiner
† cited by third party

*Primary Examiner* — Qiuwen Mi
(74) *Attorney, Agent, or Firm* — K&L Gates LLP (57) ABSTRACT

Use of a pomegranate skin extract for use in the treatment of metabolic syndrome, more particularly, fatty liver disease. More particularly, the pomegranate skin extract is used in inhibiting body weight gain in the prevention and/or the treatment of fatty liver disease in mammals.

10 Claims, 7 Drawing Sheets

POMEGRANATE SKIN EXTRACT FOR TREATING FATTY LIVER

CROSS REFERENCE TO RELATED APPLICATIONS

The present application is a National Stage of International Application No. PCT/CN2014/070408, filed on Jan. 9, 2014, the entire contents of which are being incorporated herein by reference.

TECHNICAL FIELD

The invention relates to the use of a pomegranate skin extract for use in the treatment of metabolic syndrome, more particularly, fatty liver disease.

BACKGROUND OF THE INVENTION

The pomegranate, *Punica granatum* L., is an ancient, mystical, unique fruit borne on a small, long-living tree cultivated throughout the Mediterranean region, as far north as the Himalayas, in Southeast Asia, and in California and Arizona in the United States. In addition to its ancient historical uses, pomegranate is used in several systems of medicine for a variety of ailments. Pomegranate constituents appear to act in a synergistic manner. In the past decade, numerous studies on the anti-oxidant, anti-carcinogenic, and anti-inflammatory properties of pomegranate constituents have been published, focusing on treatment and prevention of cancer, cardiovascular disease, dental conditions, bacterial infections and antibiotic resistance, and ultraviolet radiation-induced skin damage. Additionally, most studies of pomegranate have been focused on leaf, flower and seed. However, since pomegranate juice products have become more and more popular in Western countries, pomegranate skin as a waste product of juice, has not yet received some interest.

It is therefore an object of the invention to provide useful applications for pomegranate skin, especially in the field of metabolic syndrome treatment.

SUMMARY OF THE INVENTION

In one aspect of the invention, there is provided a pomegranate skin extract for use in the prevention and/or the treatment of fatty liver disease in mammals.

In a preferred embodiment of the invention, the pomegranate skin extract comprises at least 30% of punicalagin.

These and other aspects, features and advantages of the invention will become more apparent to those skilled in the art from the detailed description of embodiments of the invention, in connection with the attached drawings.

BRIEF DESCRIPTION OF THE DRAWINGS

FIG. 4 relates to the effect of PE supplement and HFD on rat liver oxidative status. Liver proteins were extracted and carbonyl protein was measured as protein oxidation markers. GSH was measured using liver homogenates. (A) carbonyl protein image; (B) Relative GSH content. Values are mean±SEM, N=15. *$p<0.05$, **$p<0.01$ vs. Normal control, ^$p<0.05$, ^^$p<0.01$ vs. HFD control.

FIG. 6 relates to the effect of PE supplement and HFD on rat live mitochondrial dynamic activities. Liver mRNA were extracted and mitochondrial dynamic related genes were analyzed by real-time PCR, proteins were extracted and analyzed by western blot. (A) real-time PCR of Mfn1, Mfn2, OPAL Drp1, Fis1; (B) western blot image of Mfn1, Mfn2, OPAL Drp1. Values are mean±SEM, N=15. *$p<0.05$, **$p<0.01$ vs. Normal control, ^$p<0.05$, ^^$p<0.01$ vs. HFD control.

FIG. 7 relates to the toxicity of pomegranate skin extract on immune system and kidney. Effects on (A) blood lymphocytes (LYM), (B) white blood cell (WBC) number and kidney function markers (C) blood urea nitrogen (BUN) and (D) creatinine (CREA) were assessed. Values are mean±SEM, N=3.5. *$p<0.05$, **$p<0.01$.

DETAILED DESCRIPTION OF THE INVENTION

The present invention relates to a pomegranate skin extract for use in the prevention and/or the treatment of fatty liver disease in mammals.

By "pomegranate skin extract", it is intended an extract obtained from pomegranate skin (also called pomegranate rind or pomegranate peel).

Preferably, this extract comprises at least 30%, preferably 40%, more preferably 50%, more still more preferably 60% of punicalagin.

As used in this specification, the words "comprises", "comprising", and similar words, are not to be interpreted in an exclusive or exhaustive sense. In other words, they are intended to mean "including, but not limited to".

The pomegranate skin extract according to the invention can be obtained by extracting pomegranate skin with a water-alcohol solution, such as an aqueous solution of ethanol. Preferably, such a solution comprises from 0 to 35% by volume of ethanol.

As an example, the extract can be prepared by:
Crushing the raw material (pomegranate skin),
Extracting the raw material with an aqueous solution of ethanol at a temperature from 40 to 80° C.,
Concentrating, filtering and separating the resulting extract using column chromatography.

Figure 2:
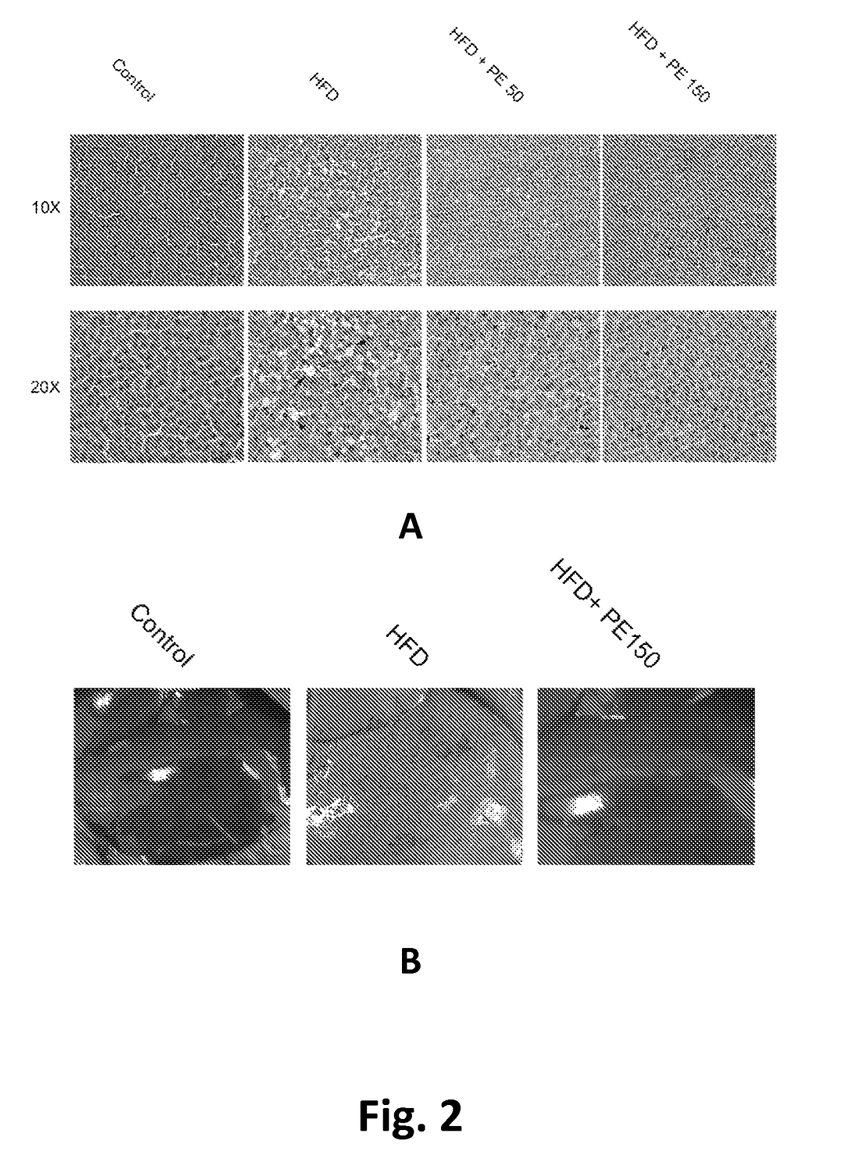
FIG. 2 shows pictures of fresh liver tissue. Liver tissue was collected after rats were sacrificed. Pictures of fresh tissues were taken (B), and then fixed with paraformaldehyde for HE staining (A).

By "fatty liver disease", it is meant a reversible condition wherein large vacuoles of triglyceride fat accumulate in liver cells (see FIG. 2). This disease can have multiple causes, such as an excessive alcohol intake or obesity (with or without effects of insulin resistance). More particularly, body weight gain may be one of the symptoms of fatty liver disease.

The pomegranate skin extract according to the invention is used in inhibiting body weight gain in a method of prevention and/or treatment of fatty liver disease.

Thus, the pomegranate skin extract according to the invention can be used for the prevention and/or the treatment of patients suffering from fatty liver disease.

For patients suffering from fatty liver disease and in particular for patients with non-alcoholic fatty liver disease, a gradual weight loss is often the only recommendation.

The inhibition of the body weight gain in a mammal can be measured by:
Weighing the mammal before the administration of the pomegranate extract,
Administering the pomegranate extract without changing the diet of the mammal,
Weighing the mammal after the administration of the pomegranate extract.

Preferably, the administration of the pomegranate extract is made daily at a dose of from 1 to 50 mg/kg/day, preferably at a dose from 5 to 30 mg/kg/day. Additionally, the time during the two weighings is preferably one week, more preferably one month. Preferably, the weighings are performed periodically, such as weekly or monthly.

Advantageously, it has been shown that the pomegranate skin extract according to the invention inhibits body weight gain and liver weight gain in a mammal having a high fat diet.

More particularly, the pomegranate skin extract according to the invention can:
inhibit steatosis, and/or
decrease the expression level of liver function markers ALT and AST, By steatosis, it is intended an abnormal retention of lipids within a cell.

The pomegranate skin extract is administered to a mammal, preferably a human. Such administration is particularly advantageous when the human has a high fat diet and/or has a body mass index equal to or above 25.

Such administration is also particularly meant for patients suffering from non-alcoholic fatty liver disease, in particular for patients suffering from non-alcoholic fatty liver disease with pure steatosis and no inflammation. Indeed, it has been shown that PE supplement significantly inhibits body weight gain even when food intake is not decreased. The pomegranate skin extract was also found to significantly inhibit lipogenesis, in particular by inhibiting SREBP1 levels and lipogenesis related gene expression. Such genes are for example fatty acid synthase (Fas), Acetyl-CoA carboxylase (ACC1), Stearoyl-CoA desaturase-1 (SCD1).

Preferably, the pomegranate skin extract is administered orally. Such administration can be performed via foods, drinks, dietary supplements or pharmaceutical compositions. In particular, the pomegranate skin extract can be added into powdered products such as powder milk, nutrition/protein powder, coffee mix/mates, chocolate/cocoa powder, tea, cheese powder, sugar, sweetener.

Advantageously, the pomegranate skin extract is administered at a dose from 1 to 50 mg/kg/day, preferably at a dose from 5 to 30 mg/kg/day.

The invention is further described with reference to the following examples. It will be appreciated that the invention as claimed is not intended to be limited in any way by these examples.

EXAMPLE

Effects of Pomegranate Extract (PE) on Fatty Liver Formation

This example describes how PE treatment demonstrated a protective effect on fatty liver formation. Therefore, liver tissues were taken and weighed. Then various tests were used to explore the protective effect of PE on fatty liver. In particular, liver function markers (ALT and AST) were quantified. Also, oxidative status and mitochondrial function, parameters that may be indicative of fatty liver formation were also analyzed; and the SREBP1 (Sterol Regulatory Element-Binding Protein 1)-mediated lipogenesis pathway was tested for possible mechanism for the observed differences in lipid metabolism and mitochondrial activity of the current study due to the HFD diet and PE treatment.

1. Materials and Methods
1.1 Pomegranate Extract (PE) Preparation

Pomegranate extract (PE) powder was produced from pomegranate skin by TianJing JF-Natural. The pomegranate extract was standardized to 40% punicalagin (dry weight). Only water and ethanol were used during the entire extraction process.

1.2 Animals

Male 30-day old Sprague-Dawley rats weighing 180-200 g were purchased from a commercial breeder (SLAC, Shanghai) and were housed in an SPF (specific parasite free) environment at 22° C. with a 12 hours light-dark cycle. All the rats were fed with chow diets for 7 days to allow adaptation to the environment and diet. The overweight body model was made by feeding rats with a high fat (HF) diet (15% saturated fat, 1% cholesterol, 84% chow diet). The rats fed with the high fat were randomly sub-divided into HF control group, HF+Low Pomegranate extract group (50 mg PE/kg body weight, resulting in a dose of 20 mg punicalagin/kg body weight), and HF+high Pomegranate extract group (150 mg PE/kg body weight, resulting in a dose of 60 mg punicalagin/kg body weight). The control group was fed with the chow diet. Each group had 15 animals. The pomegranate extract was administered at the same time with HF diet (HFD). The rat body weights and their food consumptions were recorded twice a week. The rats were sacrificed 2 months after Pomegranate extract and HF diet feed, and blood, liver, muscle and adipose tissues were collected and frozen at −75° C. Rat body weight was used as the most important index for evaluating the effect of pomegranate extract.

1.3 ALT/AST Assay

After the rats were sacrificed, blood samples were obtained by cardiac puncture, and the serum was separated by centrifugation (3,000 rpm, 10 min). The levels of alanine transaminase (ALT), aspartate transaminase (AST), were analyzed using an automated biochemistry analyzer (Hitachi Ltd., Tokyo, Japan).

1.4 GSH Assay

GSH levels were measured with 2,3-naphthalene dicarboxyaldehyde (NDA) by a published method [8]. A 20 µl sample and 180 µl of NDA derivatization solution (50 mM Tris, pH 10, 0.5 N NaOH, and 10 mM NDA in Me$_2$SO, v/v/v 1.4/0.2/0.2) were added to each well of a 96-well plate. The plate was covered to protect the wells from room light and allowed to incubate at room temperature for 30 min. The NDA-GSH fluorescence intensity was measured (472 ex/528 em) with a fluorescence plate reader (Wallac 1420; PerkinElmer Life Sciences, Wellesley, Mass.).

1.5 Real-time PCR

Total RNA was extracted from liver samples using Trizol reagent (Invitrogen) according to the manufacturer's protocol. Reverse transcription was performed using PrimeScript RT-PCR Kit (TaKaRa, DaLian, China) followed by semi-quantitative real-time PCR with specific primers. mRNA contents were normalized to mRNA of 18SRNA as housekeeping gene and expressed as relative values using the $2^{-\Delta\Delta CT}$ method.

1.6 Carbonyl Protein Assay

Liver samples were lysed with Western and IP lysis buffer (Beyotime, Jiangsu, China). The lysates were homogenized and protein concentrations were determined by the BCA Protein Assay kit. Protein carbonyls in soluble liver proteins were assayed with the Oxyblot protein oxidation detection kit (Chemicon International, Temecula, Calif.). Protein carbonyls were labeled with 2,4-dinitrophenylhydrazine (DNPH) and detected by Western blot.

1.7 Mitochondrial Complex Activity Assay

NADH-CoQ oxidoreductase (Complex I) activity was assayed by monitoring the reduction of 2,6-dichloroindophenol indophenol (DCPIP) at 600 nM upon addition of assay buffer (10× buffer containing 0.5 M Tris-HCl, pH 8.1, 1% BSA, 10 µM antimycin A, 2 mM NaN3, 0.5 mM coenzyme Q1) [1]. The final concentration of mitochondria protein was 25 µg/ml. The reaction was started by the addition of 200 µM NADH and scanned at 600 nm for 2 min. Rotenone (3 µM) was added into the reaction system as a blank control [2].

Assays of succinate-CoQ oxidoreductase (complex II), CoQ-cytochrome C reductase (complex III), and cytochrome C oxidase (complex IV) were performed as described [3-5]. Briefly, complex II was assayed in the assay buffer (10×buffer contain 0.5 M phosphate buffer, pH 8.1, 1% BSA, 10 µM antimycin A, 2 mM NaN3, 0.5 mM coenzyme Q1) with mitochondria (final concentration 25 µg/ml). The reaction was started with 10 mM succinate and scanned at 600 nm for 2 min at 30° C. Complex III was assayed by monitoring the reduction of cytochrome C at 550 nm upon the addition of assay buffer (10×buffer contains 1 M Tris-HCl, pH 7.8, 2 mM NaN3, 0.8% tween-20, 1% BSA, 2 mM decylubiquinol) with mitochondria (final concentration 10 µg/ml) and cytochrome C at 40 µM. The reaction was started by 1× assay buffer and scanned at 550 nm for 2 min. For the analysis of complex IV, assay buffer contained 50 mM phosphate buffer pH 7.0, 0.1% BSA, 0.2% tween-20, and 40 µM reduced cytochrome C. The reaction was initiated by the addition of 3 µg/ml mitochondria and scanned at 550 nm for 2 min.

Complex V activity was measured as oligomycin-sensitive, $Mg^{2+}$-ATPase activity [6]. The process was performed by measuring the increase of NADPH at 340 nm upon the addition of 10 mM HEPES pH 8.0, 20 mM succinate, 20 mM glucose, 3 mM MgCl2, 11 mM AMP, 0.75 mM NADP+, 10 mM K2HPO4, 4 u/ml hexokinase, 2 u/ml glucose-6-phosphate dehydrogenase and 60 µg/ml mitochondria [7]. The reaction was initiated by adding 1 mM ADP. All assays were performed at 30° C.

1.8 Statistical Analysis

Data are presented as means±S.E.M. Statistical significance was evaluated with one-way ANOVA followed by LSD post hoc analysis. In all comparisons, the level of significance was set at p<0.05.

2. Results

2.1 PE Supplement and HFD on Rat Overweight and Fat Accumulation

After two months of PE and HFD treatment, rats were weighed and food intake was measured. HFD could significantly induce weight gain so that the rat was overweight by about 13% and the high dose PE supplement was found to significantly decrease body weight gain due to HFD without decreasing food intake (see table 1 below).

TABLE 1

Body weight and food intake

|  | Control | High Fat Diet (HFD) | | |
| --- | --- | --- | --- | --- |
|  |  | — | Low PE | High PE |
| Initial body weight (g) | 273.1 ± 3 | 273.1 ± 3.6 | 264.3 ± 3.8 | 275.4 ± 3.2 |
| Final body weight (g) | 554.6 ± 10 | 595.9 ± 10.1* | 573.4 ± 8.5 | 570.1 ± 7.4^ |
| Body weight gain (g) | 281.5 ± 9.1 | 322.8 ± 7.3 ** | 309.1 ± 6.9 | 294.7 ± 6.7^^ |
| Food intake (g) | 28982.5 | 29381 | 28271.5 | 30547 |

2.2 PE Supplement and HFD on Rat Liver Weight

Figure 1:
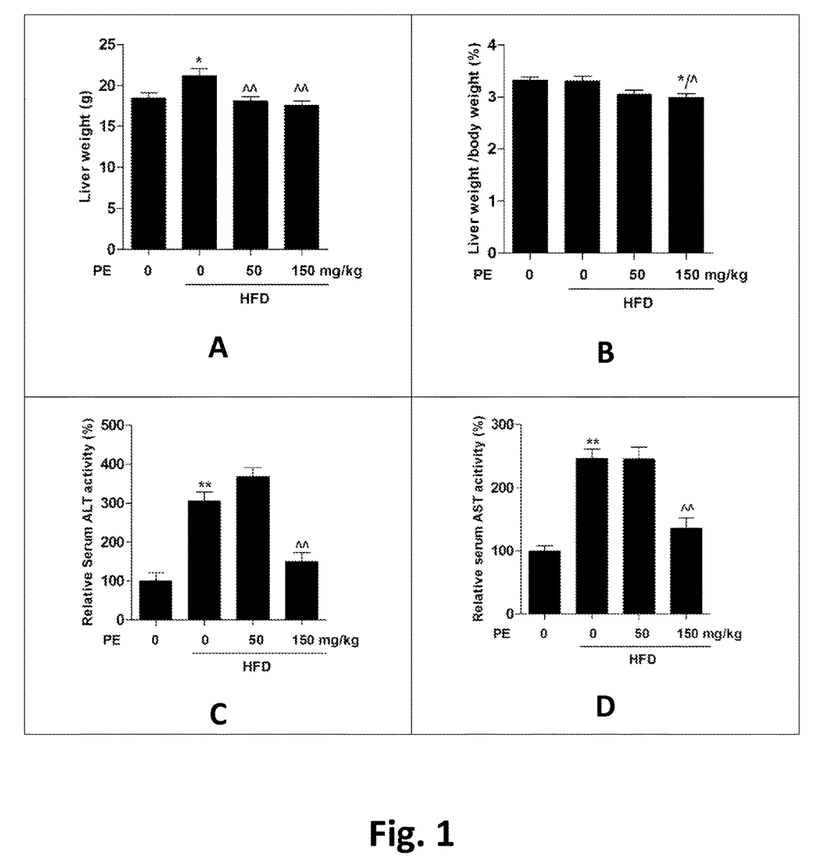
FIG. 1 shows diagrams relating to pomegranate extract (PE) supplement and high fat diet (HFD) on rat liver weight and function maker alanine aminotransferase (ALT) and aspartate aminotransferase (AST). After two months of HFD and PE treatment, rats were weighed and sacrificed, their livers were collected and weighed immediately. The results showed liver weight (A) and relative ratio to whole body weight (B). Rat serum was collected after the sacrifice, serum ALT and AST were measured. (C) relative ALT activity; (D) relative AST activity. Values are mean±SEM, N=15. *$p<0.05$, **$p<0.01$ vs. Normal control, ^$p<0.05$, ^^$p<0.01$ vs. HFD control.

HFD treatment was found to increase liver weight though the liver weight to body weight ratio was not significantly affected. Both low and high dose PE supplement were able to decrease the liver weight and the liver weight to body weight ratio significantly (FIG. 1 A, B).

2.3 PE Supplement and HFD on Rat Liver Function Maker ALT and AST

ALT and AST are commonly measured as a part of a diagnostic evaluation of hepatocellular injury, to determine liver health. The data showed that HFD could significantly increase ALT and AST content in serum (FIG. 1 C, D). Although low dose PE treatment had no obvious effect, high dose PE was found to effectively reduce serum ALT and AST content (FIG. 1 C, D).

2.4 PE Supplement and HFD on Rat Liver Lipogenesis

Figure 3:
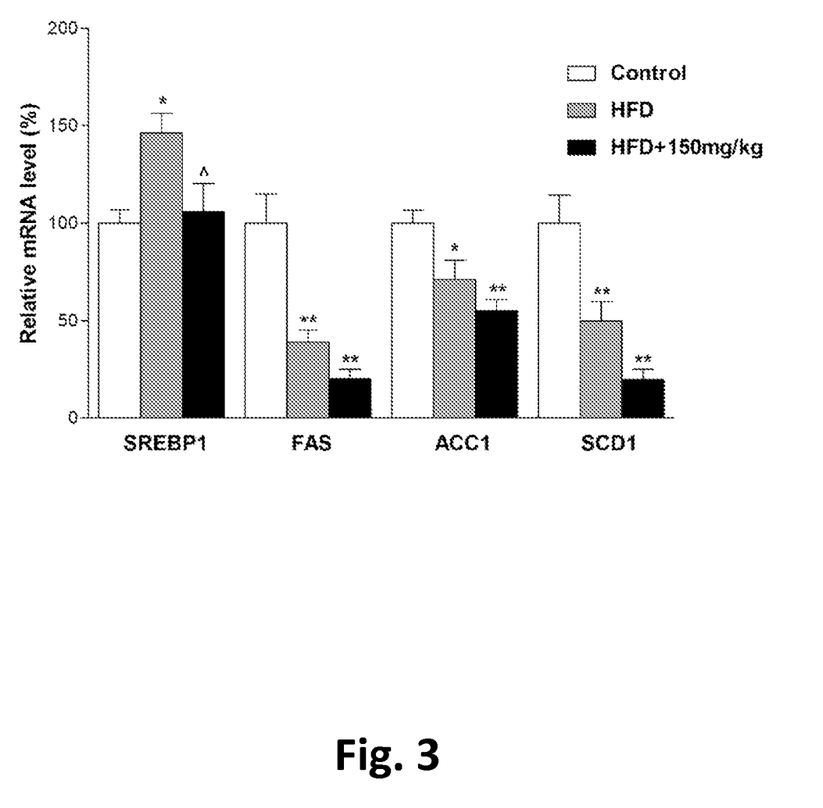
FIG. 3 shows diagrams of lipogenesis-related gene expression levels in the liver. Liver mRNA was extracted and lipogenesis related genes were analyzed by real-time PCR, proteins were extracted and SREBP1 was analyzed by western blot. Real-time PCR of SREBP1, FAS, ACC1, SCD1 are shown. Values are mean±SEM, N=15. *$p<0.05$, **$p<0.01$ vs. Normal control, ^$p<0.05$, ^^$p<0.01$ vs. HFD control.
Figure 4:
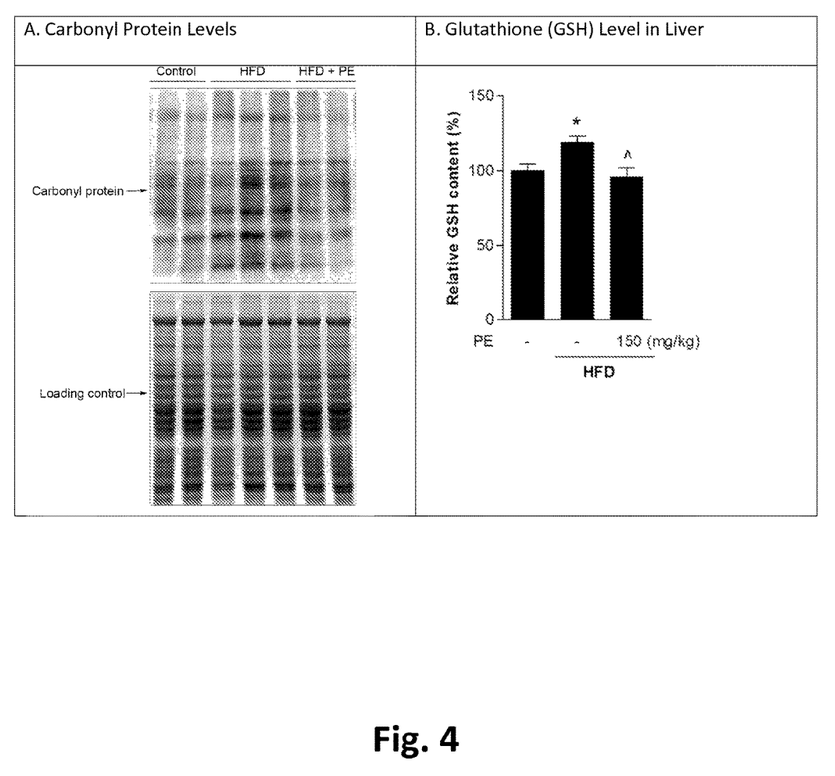

Unlike other studies, HFD failed to induce lipogenesis related genes like Fatty acid synthase (Fas), Acetyl-CoA carboxylase (ACC1), Stearoyl-CoA desaturase-1 (SCD1), although the key regulator SREBP1 mRNA was significantly increased (FIG. 4). Then protein levels of SREBP1 were tested. The precursor of SREBP1 was increased by HFD while the mature SREBP1 was not affected (FIG. 3). The results indicated that lipogenesis was not involved in HFD induced fatty liver formation. In any case, high dose PE treatment could significantly inhibit lipogenesis by decreasing SREBP1 and its target genes FAS, ACC1 and SCD1 (FIG. 3).

2.5 Effect of PE Supplement and HFD on Rat Liver Oxidative Status

We then tested the oxidative status of liver tissue. The data showed that HFD increased carbonyl protein level and that these levels were efficiently reduced by high dose PE supplement (FIG. 4A). On the contrary, instead of decrease, GSH content was significantly increased by HFD which was also restored by PE treatment (FIG. 4B).

Figure 5:
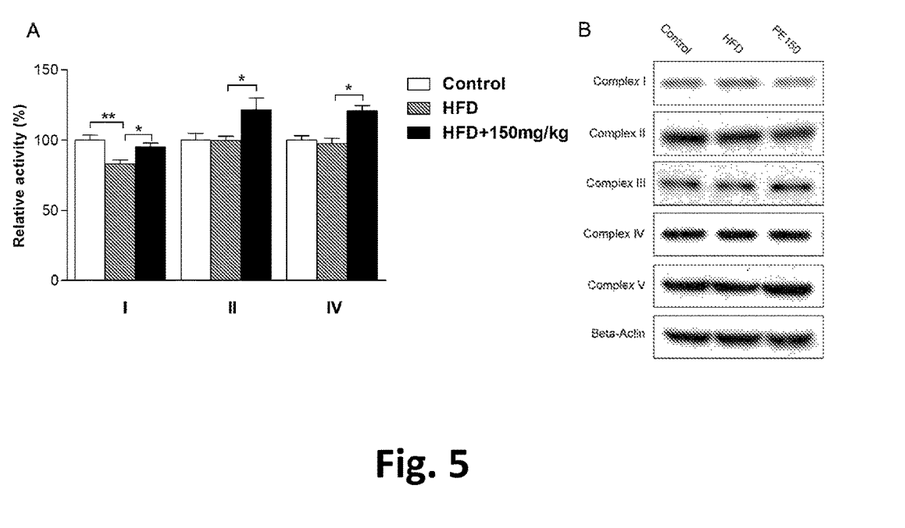
FIG. 5 relates to the effect of PE supplement and HFD on rat liver mitochondrial complex activities. Liver mitochondria were isolated and mitochondrial complex activities were analyzed. (A) Relative complex I, II, IV activities; (B) Western blot image of complex I to V. Values are mean±SEM, N=15. *$p<0.05$, **$p<0.01$ vs. Normal control, ^$p<0.05$, ^^$p<0.01$ vs. HFD control.

2.6 Effect of PE Supplement and HFD on Rat Liver Mitochondrial Complex Activities To test whether mitochondria were involved the PE protection, we first isolated liver mitochondria and analyzed mitochondrial complex activities. HFD was found to significantly decrease complex I activity (FIG. 5A) and increase complex III activity (FIG. 5B) without any effect on the other three complex activities. PE supplement was able to improve mitochondrial complex I activity compared with HFD group (FIG. 5A). Furthermore, PE could also increase complex II and IV activities (FIG. 5A). Both HFD and PE treatment had no effect on complex V activity (FIG. 5B).

2.7 PE Supplement and HFD on Rat Live Mitochondrial Dynamic Activities

Figure 6:
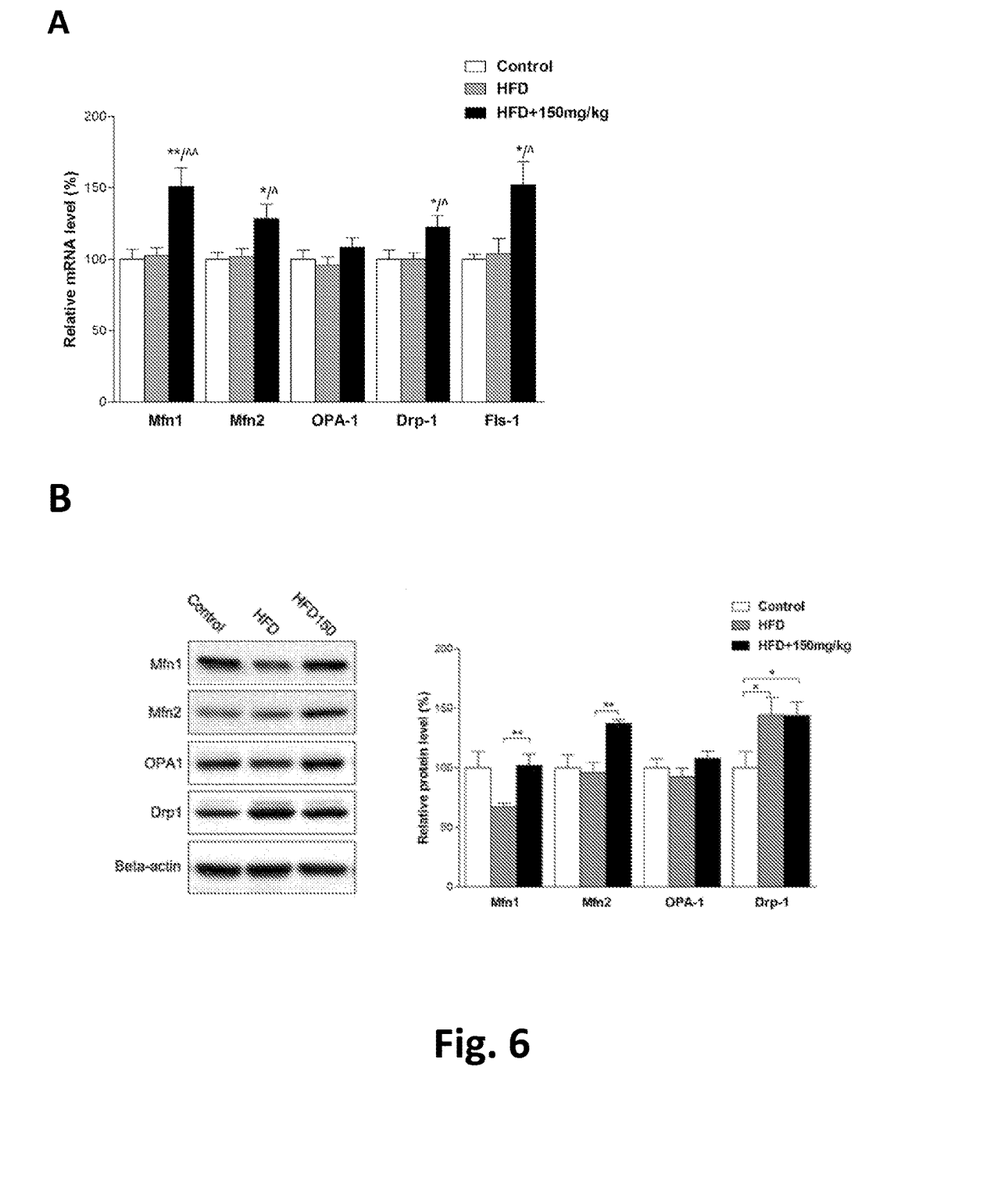

Mitochondrial dynamic activities are closely related to mitochondrial complex activities. Real-time PCR results showed that PE treatment significantly increased mRNA levels of mitochondrial fusion and fission proteins (Mfn1, Mfn2, OPA1, Drp1, Fis1) (FIG. 6A). However, Western blot results showed that Drp1 and OPA1 protein content were not affected by HFD or PE, and that Mfn1 and Mfn2 protein content was decreased by HFD and obviously increased by PE (FIG. 6B).

2.8 Toxicity of PE Supplement on Rat Immune System and Kidney

Figure 7:
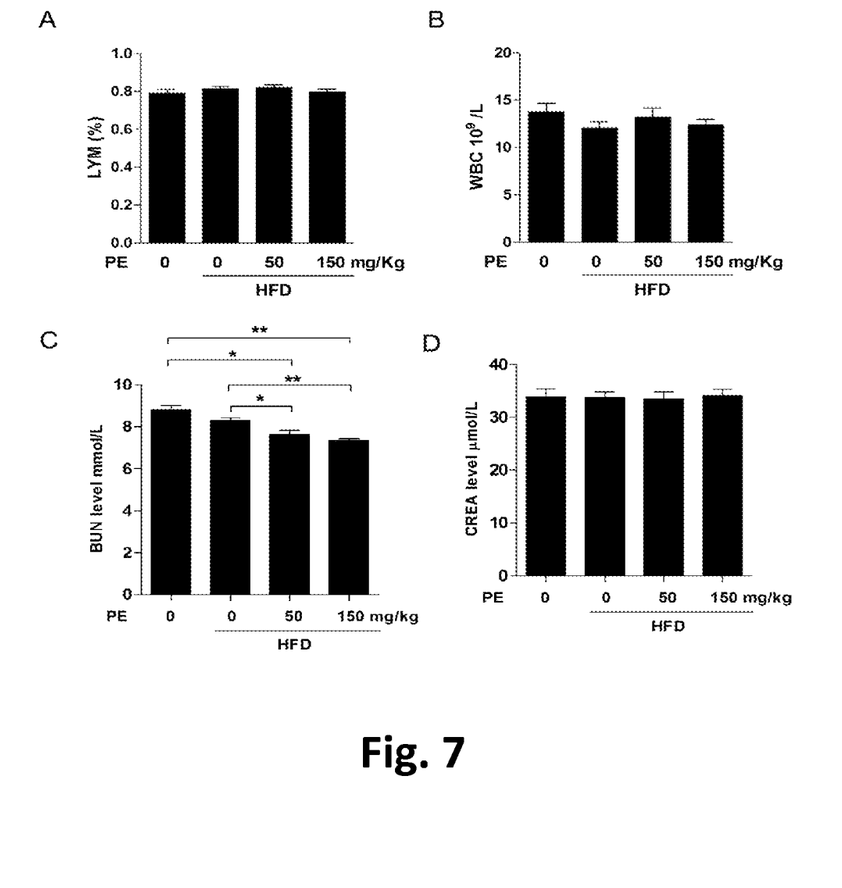

Both the HFD and the PE treatments did not elicit effects on blood lymphocytes (FIG. 7A) and white blood cells (FIG. 7B). Moreover, the HFD did not affect the kidney function markers (C) BUN and (D) CREA, whereas low- and high-dose PE significantly decreased the BUN serum levels.

CONCLUSIONS

After 8 weeks HFD treatment, rat weight and fat accumulation were significantly higher than normal diet. Low PE dose (50 mg/kg/day) and high PE dose (150 mg/kg/day) are used in the study. High dose PE was found to significantly decrease HFD induced body weight gain.

Meanwhile to make sure PE was not causing any toxicity, we tested blood cells and kidney function makers were tested. The data showed that PE supplement had no effect on blood cells. Instead of being toxic, PE was found rather to improve kidney function.

It has also been found that high dose PE treatment could efficiently decrease liver weight and liver weight to body weight ratio. Therefore, it can be assumed that decreased liver weight might be one of mechanisms through which HFD induced body weight gain is decreased by PE treatment. Both morphological picture and HE staining showed that high dose PE significantly inhibited fatty liver formation. Liver triglyceride and cholesterol were decreased by high dose PE. Liver function markers ALT and AST were restored to normal by high dose PE. All the data indicated that PE could efficiently inhibit HFD induced fatty liver formation and restore liver function to normal level.

To better understand how PE exerts the protective effect, classical SREBP1 pathway was first checked. Lipogenesis related genes like Fas, SCD1, Acc1 are activated by mature SREBP1 and involved in fatty liver formation. Unlike previous studies, these results showed that mature SREBP1 was not affected by HFD though precursor SREBP1 was significantly increased by HFD. Therefore, lipogenesis was not activated by HFD. Nevertheless, compared with the HFD group, PE treatment was found to significantly inhibit precursor SREBP1 level and lipogenesis related gene expression.

Oxidative stress status and mitochondrial function in liver were then analyzed. PE treatment could efficiently restore HFD induced carbonyl protein level and GSH level changes. Also PE treatment could inhibit HFD induced complex I activity loss. Compared with HFD group, PE treatment could significantly increase complex II and IV activities. So far, all the data indicated that PE could efficiently inhibit HFD induced fatty liver formation.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

REFERENCES

[1] Trounce, I. A.; Kim, Y. L.; Jun, A. S.; Wallace, D. C. Assessment of mitochondrial oxidative phosphorylation in patient muscle biopsies, lymphoblasts, and transmitochondrial cell lines. Methods Enzymol 264:484-509; 1996.

[2] Sun, L.; Luo, C.; Long, J.; Wei, D.; Liu, J. Acrolein is a mitochondrial toxin: Effects on respiratory function and enzyme activities in isolated rat liver mitochondria. Mitochondrion 6:136-142; 2006.

[3] Humphries, K. M.; Szweda, L. I. Selective inactivation of alpha-ketoglutarate dehydrogenase and pyruvate dehydrogenase: reaction of lipoic acid with 4-hydroxy-2-nonenal. Biochemistry 37:15835-15841; 1998.

[4] Picklo, M. J.; Amarnath, V.; McIntyre, J. O.; Graham, D. G.; Montine, T. J. 4-Hydroxy-2(E)-nonenal inhibits CNS mitochondrial respiration at multiple sites. J Neurochem 72:1617-1624; 1999.

[5] Yang, S.; Tan, T. M.; Wee, A.; Leow, C. K. Mitochondrial respiratory function and antioxidant capacity in normal and cirrhotic livers following partial hepatectomy. Cell Mol Life Sci 61:220-229; 2004.

[6] Picklo, M. J.; Montine, T. J. Acrolein inhibits respiration in isolated brain mitochondria. Biochim Biophys Acta 1535:145-152; 2001.

[7] Zheng, J.; Ramirez, V. D. Inhibition of mitochondrial proton F0F1-ATPase/ATP synthase by polyphenolic phytochemicals. Br J Pharmacol 130:1115-1123; 2000.

[8] White, C. C.; Viernes, H.; Krejsa, C. M.; Botta, D.; Kavanagh, T. J. Fluorescence-based microtiter plate assay for glutamate-cysteine ligase activity. Anal Biochem 318:175-180; 2003.

Any reference to prior art documents in this specification is not to be considered an admission that such prior art is widely known or forms part of the common general knowledge in the field.

The invention claimed is:

1. A method for inhibiting body weight gain and treating fatty liver disease in a human having the fatty liver disease and a characteristic selected from the group consisting of (i) a body mass index equal to or above 25, (ii) the fatty liver disease is non-alcoholic fatty liver disease, and (iii) a combination thereof, the method comprising administering a composition comprising pomegranate skin extract to the human.

2. The method of claim 1, wherein the composition comprises at least 30% of punicalagin.

3. The method of claim 1, wherein the composition is administered in an amount that inhibits inhibiting steatosis.

4. The method of claim 1, wherein the composition is administered in an amount that decreases the expression level of liver function markers ALT and AST.

5. The method of claim 1, wherein the human has a high fat diet.

6. The method of claim 1, wherein the human has a body mass index equal to or above 25.

7. The method of claim 1, wherein the human is a patient suffering from non-alcoholic fatty liver disease.

8. The method of claim 1, wherein the composition is administered orally.

9. The method of claim 1, wherein the oral administration is performed via a route selected from the group consisting of foods, drinks, dietary supplements and pharmaceutical compositions.

10. The method of claim 1, wherein composition is administered at a dose from 1 to 50 mg/kg/day.

\* \* \* \* \*